(12) United States Patent
Dallimore

(10) Patent No.: US 9,439,428 B2
(45) Date of Patent: Sep. 13, 2016

(54) HERBICIDAL COMPOUNDS

(71) Applicant: SYNGENTA LIMITED, Guildford, Surrey (GB)

(72) Inventor: Jonathan Wesley Paul Dallimore, Bracknell (GB)

(73) Assignee: Syngenta Limited, Guildford (GB)

( * ) Notice: Subject to any disclaimer, the term of this patent is extended or adjusted under 35 U.S.C. 154(b) by 0 days.

(21) Appl. No.: 14/701,869

(22) Filed: May 1, 2015

(65) Prior Publication Data

US 2015/0230468 A1   Aug. 20, 2015

Related U.S. Application Data

(62) Division of application No. 14/110,349, filed as application No. PCT/EP2012/056162 on Apr. 4, 2012, now Pat. No. 9,035,049.

(30) Foreign Application Priority Data

Apr. 8, 2011 (GB) .................... 1106062.1

(51) Int. Cl.
*A61K 31/50* (2006.01)
*A61K 31/501* (2006.01)
*A01N 43/58* (2006.01)
*C07D 237/14* (2006.01)
*C07D 401/04* (2006.01)

(52) U.S. Cl.
CPC ............. *A01N 43/58* (2013.01); *A61K 31/501* (2013.01); *C07D 237/14* (2013.01); *C07D 401/04* (2013.01)

(58) Field of Classification Search
None
See application file for complete search history.

(56) References Cited

FOREIGN PATENT DOCUMENTS

| DE | 4423934 | 3/1995 |
| EP | 0283261 | 9/1988 |
| WO | 2011/031658 | 3/2011 |

OTHER PUBLICATIONS

International Search Report, International Application No. PCT/EP2012/056162, completion date: Jun. 6, 2012.

*Primary Examiner* — Jeffrey H Murray
(74) *Attorney, Agent, or Firm* — James Cueva

(57) ABSTRACT

The present invention relates to novel herbicidal compounds of Formula (I),

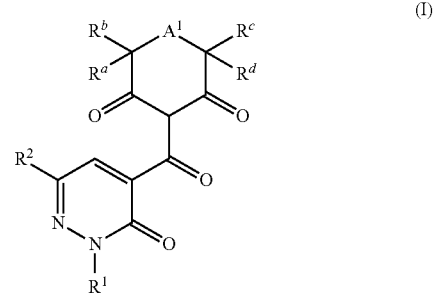

or an agronomically acceptable salt of said compound wherein $R^1$, $R^2$, $A^1$, $R^a$, $R^b$, $R^c$ and $R^d$ are as defined herein. The invention further relates to compositions which comprise the herbicidal compounds, and to their use for controlling weeds, in particular in crops of useful plants.

9 Claims, No Drawings

HERBICIDAL COMPOUNDS

This application is a divisional of U.S. application Ser. No. 14/110,349 filed Oct. 7, 2013, which is a §371 national stage entry of international application number PCT/EP2012/056162 filed Apr. 4, 2012, which claims foreign priority to GB 1106062.1 filed Apr. 8, 2011.

The present invention relates to novel herbicidal pyridazinone derivatives, to processes for their preparation, to compositions which comprise the herbicidal compounds, and to their use for controlling weeds, in particular in crops of useful plants, or for inhibiting plant growth. Herbicidal pyridine derivatives are known, for example, from EP1982978 and pyrimidone derivatives from WO2011/031658. It has now been discovered that pyridazinone derivatives exhibit advantageous herbicidal properties.

Thus, according to the present invention there is provided a herbicidal compound of Formula (I):

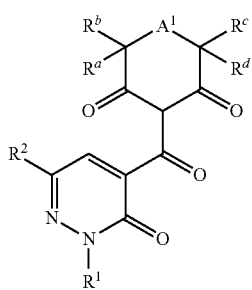

(I)

or an agronomically acceptable salt of said compound, wherein:

$R^1$ is selected from the group consisting of hydrogen, $C_1$-$C_6$alkyl, $C_1$-$C_6$haloalkyl, $C_1$-$C_3$alkoxy-$C_1$-$C_3$ alkyl, $C_1$-$C_3$ alkoxy-$C_1$-$C_3$alkoxy-$C_1$-$C_3$-alkyl, $C_1$-$C_3$alkoxy-$C_1$-$C_3$-haloalkyl, $C_1$-$C_3$-alkoxy-$C_1$-$C_3$-alkoxy-$C_1$-$C_3$-haloalkyl, $C_4$-$C_6$-oxasubstituted cycloalkoxy-$C_1$-$C_3$-alkyl, $C_4$-$C_6$-oxasubstituted cycloalkyl-$C_1$-$C_3$-alkoxy-$C_1$-$C_3$-alkyl, $C_4$-$C_6$-oxasubstituted cycloalkoxy-$C_1$-$C_3$-haloalkyl, $C_4$-$C_6$-oxasubstituted cycloalkyl-$C_1$-$C_3$-alkoxy-$C_1$-$C_3$-haloalkyl, ($C_1$-$C_3$ alkanesulfonyl-$C_1$-$C_3$ alkylamino)-$C_1$-$C_3$ alkyl, ($C_1$-$C_3$alkanesulfonyl-$C_3$-$C_4$ cycloalkylamino)-$C_1$-$C_3$alkyl, $C_1$-$C_6$alkylcarbonyl-$C_1$-$C_3$alkyl, $C_3$-$C_6$cycloalkyl-$C_2$-$C_6$alkenyl, $C_2$-$C_6$alkynyl, $C_2$-$C_6$-alkenyl, $C_2$-$C_6$-haloalkenyl, cyano-$C_1$-$C_6$-alkyl, arylcarbonyl-$C_1$-$C_3$-alkyl (wherein the aryl may be optionally substituted with one or more substituents from the group consisting of halo, $C_1$-$C_3$-alkoxy, $C_1$-$C_3$-alkyl, $C_1$-$C_3$ haloalkyl), aryl-$C_1$-$C_6$alkyl, aryloxy-$C_1$-$C_6$alkyl (wherein both cases the aryl may be optionally substituted with one or more substituents from the group consisting of halo, $C_1$-$C_3$-alkoxy, $C_1$-$C_3$-alkyl, $C_1$-$C_3$ haloalkyl), and a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more substituents selected from the group consisting of $C_1$-$C_3$alkyl, $C_1$-$C_3$haloalkyl, $C_1$-$C_3$alkenyl, $C_1$-$C_3$alkynyl, $C_1$-$C_3$ alkoxy, $C_1$-$C_3$ haloalkoxy, $C_1$-$C_6$alkyl-S(O)p-, $C_1$-$C_6$haloalkyl-S(O)p-, aryl, aryl-S(O)p, heteroaryl-S(O)p, aryloxy, heteroaryloxy, $C_1$-$C_3$ alkoxycarbonyl, $C_1$-$C_3$ alkylamino-S(O)p-, $C_1$-$C_3$ alkylamino-S(O)p-$C_1$-$C_3$ alkyl, $C_1$-$C_3$ dialkylamino-S(O)p-, $C_1$-$C_3$ dialkylamino-S(O)p-$C_1$-$C_3$ alkyl, $C_1$-$C_3$ alkylaminocarbonyl-, $C_1$-$C_3$ alkylaminocarbonyl-$C_1$-$C_3$ alkyl, $C_1$-$C_3$ dialkylaminocarbonyl, $C_1$-$C_3$ dialkylaminocarbonyl-$C_1$-$C_3$ alkyl, $C_1$-$C_3$ alkylcarbonylamino, $C_1$-$C_3$ alkyl-S(O)p-amino, cyano and nitro; the heteroaryl substituents containing one to three heteroatoms each independently selected from the group consisting of oxygen, nitrogen and sulphur, and wherein the aryl or heteroaryl component may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, phenyl, cyano and nitro;

$R^2$ is selected from the group consisting of hydrogen, halogen, cyano, nitro, $C_1$-$C_6$alkyl, $C_3$-$C_6$cycloalkyl, $C_2$-$C_6$-alkenyl, $C_2$-$C_6$alkynyl, $C_1$-$C_6$haloalkyl, $C_1$-$C_6$alkoxy, $C_1$-$C_3$haloalkoxy, $C_1$-$C_6$alkoxy-$C_1$-$C_3$ alkyl, $C_1$-$C_6$alkyl-S(O)p- and $C_1$-$C_6$haloalkyl-S(O)p-;

p=0, 1 or 2;

$A^1$ is selected from the group consisting of O, C(O) and (CR$^e$R$^f$); and $R^a$, $R^b$, $R^c$, $R^d$, $R^e$ and $R^f$ are each independently selected from the group consisting of hydrogen and $C_1$-$C_4$alkyl wherein $R^a$ and $R^c$ may together form a $C_1$-$C_3$alkylene chain.

Halogen encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Suitable alkylenyl radicals include, for example CH$_2$, CHCH$_3$, C(CH$_3$)$_2$, CH$_2$CHCH$_3$, CH$_2$CH(C$_2$H$_5$).

Suitable haloalkenyl radicals include alkenyl groups substituted one or more times by halogen, halogen being fluorine, chlorine, bromine or iodine and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Preferred $C_2$-$C_6$alkenyl radicals substituted once, twice or three times by halogen are those having a chain length of from 2 to 5 carbon atoms. Suitable haloalkylalkynyl radicals include, for example, alkylalkynyl groups substituted one or more times by halogen, halogen being bromine or iodine and, especially, fluorine or chlorine, for example 3-fluoropropynyl, 5-chloropent-2-yn-1-yl, 5-bromopent-2-yn-1-yl, 3,3,3-trifluoropropynyl and 4,4,4-trifluoro-but-2-yn-1-yl. Preferred alkylalkynyl groups substituted one or more times by halogen are those having a chain length of from 3 to 5 carbon atoms.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl, preferably methoxycarbonyl, ethoxycarbonyl or tert-butoxycarbonyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamino or a butylamino isomer. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms.

Cycloalkylamino or dicycloalkylamino is for example cyclohexylamino or dicyclopropylamino.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthioalkyl groups preferably have from 1 to 6 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

Three- to ten-membered mono- or bicyclic ring system may be aromatic, saturated or partially saturated and can contain from 1 to 4 heteroatoms each independently selected from the group consisting of nitrogen, oxygen and sulphur the ring system being optionally substituted by one or more substituents independently selected from the group consisting of $C_1$-$C_3$alkyl, $C_1$-$C_3$haloalkyl, $C_1$-$C_3$alkenyl, $C_1$-$C_3$alkynyl, $C_1$-$C_3$ alkoxy, $C_1$-$C_3$ haloalkoxy, $C_1$-$C_6$alkyl-S(O)p-, $C_1$-$C_6$haloalkyl-S(O)p-, aryl, aryl-S(O)p, heteroaryl-S(O)p, aryloxy, heteroaryloxy, $C_1$-$C_3$ alkoxycarbonyl, $C_1$-$C_3$ alkylamino-S(O)p-, $C_1$-$C_3$ alkylamino-S(O)p-$C_1$-$C_3$ alkyl, $C_1$-$C_3$ dialkylamino-S(O)p-, $C_1$-$C_3$ dialkylamino-S(O)p-$C_1$-$C_3$ alkyl, $C_1$-$C_3$ alkylaminocarbonyl-, $C_1$-$C_3$ alkylaminocarbonyl-$C_1$-$C_3$ alkyl, $C_1$-$C_3$ dialkylaminocarbonyl, $C_1$-$C_3$ dialkylaminocarbonyl-$C_1$-$C_3$ alkyl, $C_1$-$C_3$ alkylcarbonylamino, $C_1$-$C_3$ alkyl-S(O)p-amino, cyano and nitro. Such ring systems thus include, for example, cycloalkyl, phenyl, heterocyclyl and heteroaryl. Examples of "partially saturated" rings include, for example, 1,4 benzodioxin and 1,3 benzodioxole.

Cycloalkyl groups preferably have from 3 to 6 ring carbon atoms and may be substituted by one or more methyl groups; they are preferably unsubstituted, for example cyclopropyl, cyclobutyl, cyclopentyl or cyclohexyl.

Aryl includes benzyl, phenyl, including phenyl as part of a substituent such as phenoxy, benzyl, benzyloxy, benzoyl, phenylthio, phenylalkyl, phenoxyalkyl or tosyl, may be in mono- or poly-substituted form, in which case the substituents may, as desired, be in the ortho-, meta- and/or para-position(s).

Heterocyclyl, for example, includes morpholinyl, tetrahydrofuryl.

Heteroaryl, including heteroaryl as part of a substituent such as heteroaryloxy, means, for example, a five or six member heteroaryl containing one to three heteroatoms, each independently selected from the group consisting of oxygen, nitrogen and sulphur. It should be understood that the heteroaryl component may be optionally mono or poly substituted. The term heteroaryl thus includes, for example, furanyl, thiophenyl, thiazolyl, oxazolyl, isoxazolyl, thiazolyl, pyrazolyl, isothiazolyl, pyridyl, pyridazinyl, pyrazinyl, pyrimidinyl and triazolyl.

Compounds of Formula I may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula I may be in equilibrium with alternative hydroxyl tautomeric forms. It should be appreciated that all tautomeric forms (single tautomer or mixtures thereof), racemic mixtures and single isomers are included within the scope of the present invention.

In one embodiment $R^1$ is selected from the group consisting of hydrogen, $C_1$-$C_6$alkyl, $C_1$-$C_6$haloalkyl, $C_1$-$C_3$alkoxy$C_1$-$C_3$alkyl, $C_1$-$C_3$alkoxy $C_2$-$C_3$alkoxy $C_1$-$C_3$alkyl, $C_1$-$C_6$haloalkyl, $C_2$-$C_6$haloalkenyl, and $C_1$-$C_3$alkoxy-$C_1$-$C_3$haloalkyl.

In another preferred embodiment $R^1$ is aryl, preferably phenyl, or a 5 or 6-membered heteroaryl containing one to three heteroatoms each independently selected from the group consisting of oxygen, nitrogen and sulphur, and wherein the aryl or heteroaryl may be optionally substituted by one or more substituents selected from the group consisting of halo, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)p-, $C_1$-$C_6$haloalkyl-S(O)p-, cyano and nitro. Especially preferred is wherein $R^1$ is an optionally substituted aryl selected from the group consisting of phenyl, phenoxy, phenoxy-$C_1$-$C_6$alkyl, benzyl, thiophenyl, 1,4 benzodioxinyl, 1,3 benzodioxoleyl and pyridyl, most preferably an optionally substituted phenyl or pyridyl.

In another preferred embodiment $R^2$ is selected from the group consisting of hydrogen, $C_1$-$C_6$ alkyl (preferably methyl), halogen (preferably chlorine), $C_2$-$C_6$ alkoxy (preferably methoxy), $C_1$-$C_6$ haloalkyl preferably $CF_3$) and CN. In a more preferred embodiment $R^2$ is hydrogen of methyl.

In another embodiment $A^1$ is $CR^eR^f$ and wherein $R^a$, $R^b$, $R^c$, $R^d$, $R^e$ and $R^f$ are hydrogen. In another embodiment of the present invention $A^1$ is $CR^eR^f$, wherein $R^b$, $R^d$, $R^e$ and $R^f$ are hydrogen, $R^a$ and $R^c$ together form an ethylene chain.

The present invention also includes agronomically acceptable salts that the compounds of Formula I may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a micro emulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Fourteenth Edition, British Crop Protection Council, 2006.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide. These safeners have shown particularly good results in maize and/or cereals such as wheat and barley when higher rates (e.g >50 g/ha) of compounds of Formula (I) are used.

The safeners of the compound of Formula I may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phos-phonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf Maize is particularly preferred.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared using the following methods.

Preparation of compounds of the present invention is outlined in the following schemes.

Preparation of compounds Formula (I) is carried out analogously to known processes (for example those described in WO97/46530, EP0353187 and U.S. Pat. No. 6,498,125) and comprises reacting a compound of the following formula:

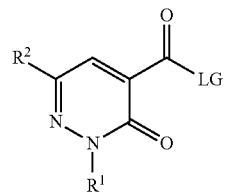

(3b)

where the definitions of $R^1$ and $R^2$ are as for Formula (I) and LG is a suitable leaving group, for example a halogen atom, such as chlorine, or an alkoxy or aryloxy group, such as 4-nitrophenoxy, in an inert organic solvent, such as dichloromethane or acetonitrile, in the presence of a base, such as triethylamine, with compounds

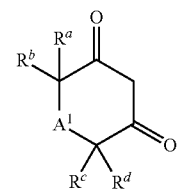

wherein
$A^1$ and $R^a$, $R^b$, $R^c$, $R^d$ are as defined previously;
to give the following esters (3a):

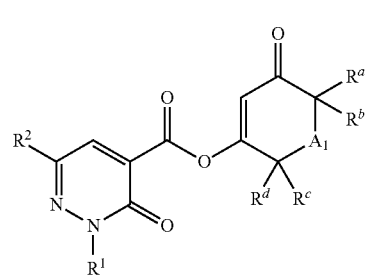

(3a)

which may be rearranged using catalysts, such as 4-dimethylaminopyridine, or acetone cyanohydrin, or a metal cyanide salt, such as sodium cyanide, in the presence of a suitable base, such as triethylamine, to give compounds of Formula (I), as shown in Scheme 1. It is advantageous to have a dehydrating agent, such as molecular sieves, present in the reaction medium to ensure any water initially present in the solvent or associated with the other components of the reaction mixture is prevented from causing any unwanted hydrolysis of intermediates.

EXAMPLES

The following non-limiting preparation examples are provided. Abbreviations as used in the following Examples are as follows: s=singlet, d=doublet, t=triplet, m=multiplet, bs=broad signal, bm=broad multiplet, dd=double doublet, dt=double triplet, td=triple doublet and dq=double quartet.

Example 1

Preparation of 2-(3-Oxo-2-phenyl-2,3-dihydropyridazine-4-carbonyl)-cyclohexane-1,3-dione (Compound 1.1)

3-Oxo-2-phenyl-2,3-dihydropyridazine-4-carboxylic acid (0.52 g, 2.42 mmol) was stirred in anhydrous dichloromethane (13 ml) and 1 drop of anhydrous dimethylformamide was added. Oxalyl chloride (0.25 mL, 2.90 mmol) was added dropwise to the suspension resulting in a brown solution. After 1.5 h the reaction was concentrated in vacuo. The residue obtained was dissolved in dichloromethane (20 ml). To the brown solution anhydrous triethylamine (1 ml), then cyclohexanedione (0.33 g, 2.90 mmol) was added, producing a reddish coloured solution. A further 0.33 ml of anhydrous triethylamine was added. The reaction mixture was stirred at room temperature for 2 h (reaction monitored by LCMS), then acetone cyanohydrin (1 drop) and anhydrous triethylamine (0.67 ml) was added and the reaction mixture was stirred overnight. LCMS indicated the desired product had been formed. The reaction mixture was concentrated in vacuo. The residue obtained was purified using column chromatography (SiO$_2$, Toluene/Triethylamine/Dioxane/EtOH/Water 100:40:20:20:5 by volume), and then further purified by column chromatography (SiO2, hexane/ethyl acetate/acetic acid 2:1:0.02 to 0:100:2) to afford the title compound as an orange oil (25 mg, 3% yield). $^1$H NMR (CDCl$_3$) 2.04 (m, 2H), 2.61 (br s, 4H), 7.18 (d, 1H) 7.46 (m, 2H), 7.59 (m, 3H) 7.96 (d, 1H) ppm.

Example 2

Preparation of 2-(6-Methyl-3-oxo-2-phenyl-2,3-dihydropyridazine-4-carbonyl)-cyclohexane-1,3-dione (Compound 1.2)

6-Methyl-3-oxo-2-phenyl-2,3-dihydropyridazine-4-carboxylic acid (0.56 g, 2.42 mmol) was stirred in anhydrous dichloromethane (13 ml) and 1 drop of anhydrous dimethylformamide was added. Oxalyl chloride (0.25 mL, 2.90 mmol) was added dropwise to the yellow solution. After 1.5 h the reaction was concentrated in vacuo. The residue obtained was dissolved in dichloromethane (20 ml). To the brown solution anhydrous triethylamine (1 ml), then cyclohexanedione (0.33 g, 2.90 mmol) was added, producing a reddish solution. A further 0.33 ml of anhydrous triethylamine was added. The reaction mixture was stirred at room temperature for 2 h (reaction monitored by LCMS), then acetone cyanohydrin (1 drop) and anhydrous triethylamine (0.67 ml) was added and the reaction was stirred overnight. LCMS indicated the desired product had been formed. The reaction mixture was concentrated in vacuo. The residue obtained was purified using column chromatography (SiO$_2$, Toluene/Triethylamine/Dioxane/EtOH/Water 100:40:20:20:5 by volume) to afford the title compound as an orange oil (382 mg, 49%). $^1$H NMR (CDCl$_3$) 2.05 (quin, 2H), 2.41 (m, 3H), 2.47 (br s, 2H), 2.73 (br s, 2H), 7.10 (s, 1H), 7.36 (m, 1H), 7.46 (m, 2H), 7.57 (m, 2H), 16.15 (br s, 1H) ppm.

TABLE 1

Examples of herbicidal compounds of the present invention.

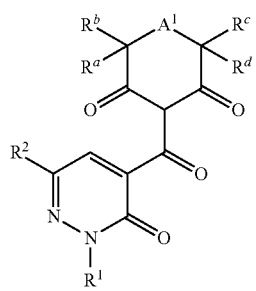

(I)

| Cmp | A$^1$ | R$^a$ | R$^c$ | R$^b$ | R$^d$ | R$^1$ | R$^2$ | NMR $^1$H NMR (CDCl$_3$) |
|---|---|---|---|---|---|---|---|---|
| 1.1 | CH$_2$ | H | H | H | H | Phenyl | H | 2.04 (m, 2H), 2.61 (br s, 4H), 7.18 (d, 1 H) 7.46 (m, 2 H), 7.59 (m, 3 H) 7.96 (d, 1 H) ppm. |
| 1.2 | CH$_2$ | H | H | H | H | Phenyl | CH$_3$ | 2.05 (quin, 2H), 2.41 (m, 3H), 2.47 (br s, 2H), 2.73 (br s, 2H), 7.10 (s, 1H), 7.36 (m, 1H), 7.46 (m, 2H), 7.57 (m, 2H), 16.15 (br s, 1H) ppm. |
| 1.3 | CH$_2$ | H | H | H | H | 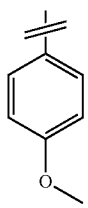 | CH$_3$ | 7.45-7.48 (2H, d), 7.03 (1H, s), 6.93-6.95 (2H, d), 3.82 (3H, s), 2.47-2.56 (4H, m), 2.38 (3H, s), 1.94-2.13 (2H, m) |

TABLE 1-continued

Examples of herbicidal compounds of the present invention.

$$\text{(I)}$$

General structure: pyridazinone substituted with R¹ on ring N, R² at position, connected via C(=O) to a cyclohexane-1,3-dione bearing A¹, Rᵃ, Rᵇ, R꜀, Rᵈ substituents.

| Cmp | A¹ | Rᵃ | R꜀ | Rᵇ | Rᵈ | R¹ | R² | NMR ¹H NMR (CDCl₃) |
|---|---|---|---|---|---|---|---|---|
| 1.4 | CH₂ | —CH₂—CH₂— | | H | H | 4-methoxyphenyl-CH= | CH₃ | 16.17 (1H, s), 7.47-7.50 (2H, m), 7.07 (1H, s), 6.94-6.96 (2H, d), 3.83 (3H, s), 3.08-3.10 (1H, br t), 2.92-2.95 (1H, br t), 2.39 (3H, s), 2.17-2.24 (6H, m) |
| 1.5 | CHCH₃ | H | H | H | H | 4-methoxyphenyl-CH= | CH₃ | 16.08 (1H, s), 7.47-7.49 (2H, d), 7.10 (1H, s), 6.94-6.96 (2H, d), 3.83 (3H, s), 2.72-2.78 (1H, br m), 2.44-2.58 (2H, br m), 2.40 (3H, s), 2.13-2.37 (2H, br m), 1.09-1.11 (3H, d) |
| 1.6 | CHCH₃ | H | H | H | H | 2-methylphenyl-CH= | CH₃ | UPLCMS, 5 min, t = 2.34 min, m/z = 353 [M + H]+ |
| 1.7 | CH₂ | —CH₂—CH₂— | | H | H | Phenyl | CH₃ | 7.39-7.55 (5H, m), 7.29-7.31 (1H, s), 2.93-3.05 (2H, broad s), 2.38-2.42 (3H, s), 2.16-2.23 (3H, m), 1.80-1.90 (2H, broad m), 1.74-1.80 (1H, m) |
| 1.8 | C=O | CH₃ | CH₃ | CH₃ | CH₃ | Phenyl | CH₃ | 7.39-7.53 (6H, m), 2.42-2.44 (3H, s), 1.38-1.45 (12H, s), |
| 1.9 | CHCH₃ | H | H | H | H | Phenyl | CH₃ | 7.38-7.55 (5H, m), 7.29-7.32 (1H, s), 2.25-2.68 (8H, broad m), 1.07-1.12 (3H, d) |
| 1.10 | CH₂ | —CH₂—CH₂— | | H | H | 6-methylpyridin-2-yl-CH= | CH₃ | 7.88 (1H, t), 7.61 (1H, d), 7.32 (1H, d), 7.13 (1H, s), 3.04 (2H, brs), 2.69 (3H, s), 2.42 (3H, s), 2.23 (1H, d), 2.16 (2H, brs), 1.90 (2H, brs), 1.73 (1H, dt). |
| 1.11 | CH₂ | H | H | H | H | 6-methylpyridin-2-yl-CH= | CH₃ | 7.95 (1H, t), 7.70 (1H, d), 7.37 (1H, d), 7.14 (1H, s), 2.73 (3H, s), 2.68-2.57 (4H, m), 2.43 (3H, s), 2.06 (2H, quintet). |
| 1.12 | C=O | CH₃ | CH₃ | CH₃ | CH₃ | 2-methylphenyl-CH= | CH₃ | 16.47 (1H, s), 7.20-7.35 (5H, m), 2.43 (3H, s), 2.21 (3H, s), 1.52 (3H, s), 1.37 (3H, s). |

TABLE 1-continued

Examples of herbicidal compounds of the present invention.

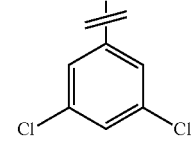
(I)

| Cmp | A¹ | Rᵃ Rᶜ | Rᵇ | Rᵈ | R¹ | R² | NMR ¹H NMR (CDCl₃) |
|---|---|---|---|---|---|---|---|
| 1.13 | CH₂ | —CH₂—CH₂— | H | H | 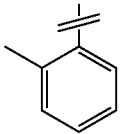 | CH₃ | 7.54 (2H, s), 7.38 (1H, s), 7.25 (1H, s), 3.06-3.14 (2H br, m) 2.23 (3H, s), 2.11-2.24 (4H, m), 1.98 (1H, m), 1.85 (1H, m) |
| 1.14 | CH₂ | —CH₂—CH₂— | H | H | 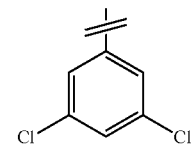 | CH₃ | 16.02 (1H, s), 7.25-7.32 (4H, m), 7.13 (1H, s), 3.08 (1H br, t), 2.82 (1H br, t), 2.4 (3H, s), 2.21 (3H, s), 1.97-2.18 (6H, m) |
| 1.15 | CH₂ | H H | H | H | 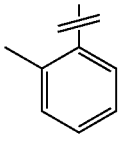 | CH₃ | 7.7 (1H, s), 7.67 (2H, s), 7.38 (1H, s), 2.87 (1H, m), 2.58 (4H, m), 2.21 (3H, s), 2.09-2.18 (2H, m) |
| 1.16 | CH₂ | H H | H | H | 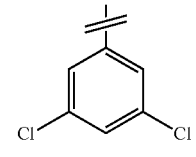 | CH₃ | 16.02 (1H, s), 7.25-7.32 (4H, m), 7.17 (1H, s), 2.71 (2H, m), 2.45 (2H, m), 2.41 (3H, s), 2.21 (3H, s), 1.98-2.06 (2H, m) |
| 1.17 | CHCH₃ | H H | H | H | 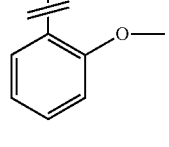 | CH₃ | 16.0 (s, 1H), 7.6 (m, 2H), 7.3 (m, 1H), 7.0 (s, 1H), 2.8 (m, 1H), 2.6 (m, 2H), 2.1 (m, 1H), 1.1 (d, 3H) |
| 1.18 | CHCH₃ | H H | H | H | 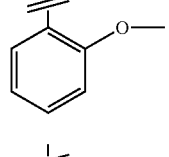 | CH₃ | 7.3 (2H, m) 7.0 (3H, m), 3.8 (3H, s), 2.5 (2H, m), 2.4 (1H, m), 2.3 (3H, s), 2.1 (2H, m), 1.2 (3H, d) |
| 1.19 | CH₂ | H H | H | H | 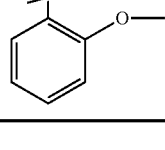 | CH₃ | 7.4 (1H, s), 7.1 (2H, s), 7.38 (2H, s), 3.8 (3H, s), 3.0 (2H, m), 2.4 (3H, s), 2.21 (2H, s), 2.07-2.15 (2H, m) |
| 1.20 | CH₂ | —CH₂—CH₂— | H | H |  | CH₃ | 7.4 (1H, s), 7.1 (2H, s), 7.38 (2H, s), 5.5 (1H, s) 3.8 (3H s), 3.0 (2H, m), 2.0 (3H, m), 2.21 (6H, s), 2.07-2.15 (3H, m) |

Biological Examples

Seeds of a variety of test species are sown in standard soil in pots (*Alopecurus myosuroides* (ALOMY), *Setaria faberi* (SETFA), *Echinochloa crus-galli* (ECHCG), *Abuthilon theophrasti* (ABUTH) and *Amaranthus retoflexus* (AMARE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds ae applied at 1000 g/h. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage herbicidal damage caused to the plant. The biological activities are shown in the following table on a five point scale (5=80-100% damage; 4=60-79% damage; 3=40-59% damage; 2=20-39% damage; 1=0-19% damage).

| | POST Application | | | | | PRE Application | | | | |
|---|---|---|---|---|---|---|---|---|---|---|
| Compound | ABUTH | AMARE | SETFA | ALOMY | ECHCG | ABUTH | AMARE | SETFA | ALOMY | ECHCG |
| 1.1 | 5 | 5 | 5 | 5 | 5 | 5 | 5 | 5 | 5 | 5 |
| 1.2 | 5 | 5 | 5 | 5 | 5 | 5 | 5 | 5 | 5 | 5 |
| 1.3 | 5 | 5 | 5 | 5 | 5 | 5 | 5 | 5 | 5 | 5 |
| 1.4 | 5 | 5 | 5 | 5 | 5 | 5 | 5 | 5 | 5 | 5 |
| 1.5 | 5 | 5 | 5 | 5 | 5 | 5 | 5 | 5 | 5 | 5 |
| 1.6 | 5 | 5 | 5 | 5 | 5 | 5 | 5 | 5 | 5 | 5 |
| 1.7 | 5 | 5 | 5 | 5 | 5 | 5 | 5 | 5 | 5 | 5 |
| 1.8 | 5 | 5 | 5 | 5 | 5 | 5 | 5 | 5 | 5 | 5 |
| 1.9 | 5 | 5 | 5 | 5 | 5 | 5 | 5 | 5 | 5 | 5 |

The invention claimed is:

1. A method of controlling weeds at a locus comprising application to the locus of a weed controlling amount of a herbicidal composition comprising a compound of Formula (I):

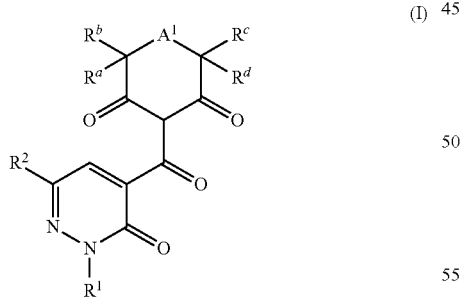

or an agronomically acceptable salt of said compound, wherein:—

$R^1$ is selected from the group consisting of hydrogen, $C_1$-$C_6$alkyl, $C_1$-$C_6$haloalkyl, $C_1$-$C_3$alkoxy-$C_1$-$C_3$alkyl, $C_1$-$C_3$alkoxy-$C_1$-$C_3$alkoxy-$C_1$-$C_3$-alkyl, $C_1$-$C_3$alkoxy-$C_1$-$C_3$haloalkyl, $C_1$-$C_3$-alkoxy-$C_1$-$C_3$-alkoxy-$C_1$-$C_3$-haloalkyl, $C_4$-$C_6$-oxasubstitutedcycloalkoxy-$C_1$-$C_3$-alkyl, $C_4$-$C_6$-oxasubstituted-cycloalkyl-$C_1$-$C_3$-alkoxy-$C_1$-$C_3$-alkyl, $C_4$-$C_6$-oxasubstitutedcycloalkoxy-$C_1$-$C_3$-alkyl, $C_4$-$C_6$-oxasubstitutedcycloalkoxy-$C_1$-$C_3$-haloalkyl, $C_4$-$C_6$-oxasubstitutedcycloalkyl-$C_1$-$C_3$-alkoxy-$C_1$-$C_3$-haloalkyl, ($C_1$-$C_3$ alkanesulfonyl-$C_1$-$C_3$alkylamino)-$C_1$-$C_3$alkyl, ($C_1$-$C_3$ alkanesulfonyl-$C_3$-$C_4$cycloalkylamino)-$C_1$-$C_3$alkyl, $C_1$-$C_6$alkylcarbonyl-$C_1$-$C_3$alkyl, $C_3$-$C_6$cycloalkyl-$C_2$-$C_6$alkenyl, $C_2$-$C_6$alkynyl, $C_2$-$C_6$-alkenyl, $C_2$-$C_6$-haloalkenyl, cyano-$C_1$-$C_6$-alkyl, arylcarbonyl-$C_1$-$C_3$-alkyl (wherein the aryl may be optionally substituted with one or more substituents from the group consisting of halo, $C_1$-$C_3$-alkoxy, $C_1$-$C_3$-alkyl, $C_1$-$C_3$haloalkyl), aryl-$C_1$-$C_6$alkyl, aryloxy-$C_1$-$C_6$alkyl (wherein both cases the aryl may be optionally substituted with one or more substituents from the group consisting of halo, $C_1$-$C_3$-alkoxy, $C_1$-$C_3$-alkyl, $C_1$-$C_3$haloalkyl), and a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more substituents selected from the group consisting of $C_1$-$C_3$alkyl, $C_1$-$C_3$haloalkyl, $C_1$-$C_3$alkenyl, $C_1$-$C_3$alkynyl, $C_1$-$C_3$alkoxy, $C_1$-$C_3$haloalkoxy, $C_1$-$C_6$alkyl-S(O)p-, $C_1$-$C_6$haloalkyl-S(O)p-, aryl, aryl-S(O)p, heteroaryl-S(O)p, aryloxy, heteroaryloxy, $C_1$-$C_3$-alkoxycarbonyl, $C_1$-$C_3$-alkylamino-S(O)p-, $C_1$-$C_3$alkylamino-S(O)p-$C_1$-$C_3$ alkyl, $C_1$-$C_3$dialkylamino-S(O)p-, $C_1$-$C_3$dialkylamino-S(O)p-$C_1$-$C_3$alkyl, $C_1$-$C_3$alkylaminocarbonyl-, $C_1$-$C_3$alkylaminocarbonyl-$C_1$-$C_3$ alkyl, $C_1$-$C_3$ dialkylaminocarbonyl, $C_1$-$C_3$dialkylaminocarbonyl-$C_1$-$C_3$alkyl, $C_1$-$C_3$alkylcarbonylamino, $C_1$-$C_3$alkyl-S(O)p-amino, cyano and nitro; the heteroaryl substituents containing one to three heteroatoms each independently selected from the group consisting of oxygen, nitrogen and sulphur, and wherein the aryl or heteroaryl component may be optionally substituted by one or more substituents selected from the group consisting of halo, $C_1$-$C_3$alkyl, $C_1$-$C_3$haloalkyl, $C_1$-$C_3$alkoxy, $C_1$-$C_3$haloalkoxy, phenyl, cyano and nitro;

$R^2$ is selected from the group consisting of hydrogen, halogen, cyano, nitro, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$alkoxy, $C_1$-$C_3$haloalkoxy, $C_1$-$C_6$alkoxy-$C_1$-$C_3$alkyl, $C_1$-$C_6$alkyl-S(O)p- and $C_1$-$C_6$haloalkyl-S(O)p-;

p is 0, 1 or 2;

$A^1$ is selected from the group consisting of O, C(O) and (CR$^e$R$^f$); and

R$^a$, R$^b$, R$^c$, R$^d$, R$^e$ and R$^f$ are each independently selected from the group consisting of hydrogen and $C_1$-$C_4$alkyl wherein R$^a$ and R$^c$ may together form a $C_1$-$C_3$alkylene chain.

2. A method according to claim 1, wherein in the compound of Formula (I) $R^1$ is selected from the group consisting of hydrogen, $C_1$-$C_6$alkyl, $C_1$-$C_6$haloalkyl, $C_1$-$C_3$alkoxy-$C_1$-$C_3$alkyl, $C_1$-$C_3$alkoxy-$C_2$-$C_3$alkoxy-$C_1$-$C_3$alkyl, $C_2$-$C_6$haloalkenyl, $C_1$-$C_3$alkoxy-$C_1$-$C_3$haloalkyl, aryl, and a 5 or 6-membered heteroaryl, the heteroaryl containing one to three heteroatoms each independently selected from the group consisting of oxygen, nitrogen and sulphur, and wherein the aryl, or heteroaryl component may be optionally substituted by one or more substituents selected from the group consisting of halo, $C_1$-$C_3$alkyl, $C_1$-$C_3$haloalkyl, $C_1$-$C_3$alkoxy, cyano and nitro.

3. A method according to claim 1, wherein in the compound of Formula (I) $R^1$ is selected from the group consisting of aryl, and a 5 or 6-membered heteroaryl, the heteroaryl containing one to three heteroatoms each independently selected from the group consisting of oxygen, nitrogen and sulphur, and wherein the aryl or heteroaryl component may be optionally substituted by one or more substituents selected from the group consisting of halo, $C_1$-$C_3$alkyl, $C_1$-$C_3$haloalkyl, $C_1$-$C_3$ alkoxy, cyano and nitro.

4. A method according to claim 1, wherein in the compound of Formula (I) $R^1$ is phenyl or pyridyl wherein the phenyl or pyridyl may be optionally substituted by one or more substituents selected from the group consisting of halo, $C_1$-$C_3$alkyl, $C_1$-$C_3$haloalkyl, $C_1$-$C_3$alkoxy, cyano and nitro.

5. A method according to claim 1, wherein in the compound of Formula (I) $A^1$ is $CR^eR^f$ and wherein $R^a$, $R^b$, $R^c$, $R^d$, $R^e$ and $R^f$ are hydrogen.

6. A method according to claim 1, wherein in the compound of Formula (I) $A^1$ is $CR^eR^f$, wherein $R^b$, $R^d$, $R^e$ and $R^f$ are hydrogen, and $R^a$ and $R^b$ together form an ethylene chain.

7. A method according to claim 1, wherein in the compound of Formula (I) $A^1$ is —$CHCH_3$ and $R^a$, $R^b$, $R^c$ and $R^d$ are hydrogen.

8. A method according to claim 1, wherein in the compound of Formula (I) $R^2$ is hydrogen or methyl.

9. A method according to claim 1, wherein the herbicidal composition further comprises at least one additional herbicide or herbicide safener.

* * * * *